United States Patent

Provonchee

[11] Patent Number: 5,670,636
[45] Date of Patent: Sep. 23, 1997

[54] FRACTIONATED AGAROID COMPOSITIONS, THEIR PREPARATION AND USE

[75] Inventor: Richard B. Provonchee, Camden, Me.

[73] Assignee: FMC Corporation, Philadelphia, Pa.

[21] Appl. No.: 44,845

[22] Filed: Apr. 8, 1993

Related U.S. Application Data

[63] Continuation-in-part of Ser. No. 537,555, Jun. 13, 1990, abandoned.

[51] Int. Cl.$^6$ ..................................................... C08B 37/12
[52] U.S. Cl. ........................ 536/123.1; 536/124; 536/127
[58] Field of Search .......................... 536/1.1, 3, 1.11, 536/123.1, 124, 127

[56] References Cited

U.S. PATENT DOCUMENTS

| | | | |
|---|---|---|---|
| 3,956,273 | 5/1976 | Guiseley | 424/361 |
| 3,959,457 | 5/1976 | Speaker et al. | 424/19 |
| 4,291,025 | 9/1981 | Pellico | 424/180 |
| 4,965,591 | 10/1990 | Kurabayashi et al. | 346/108 |
| 4,985,538 | 1/1991 | Fukuda et al. | 528/308.2 |
| 5,175,000 | 12/1992 | Godowski et al. | 424/426 |

FOREIGN PATENT DOCUMENTS 0304024  2/1989  European Pat. Off. .

*Primary Examiner*—Jeffrey C. Mullis
*Attorney, Agent, or Firm*—Anthony L. Cupoli; Richard E. Elden; Mark A. Greenfield

[57] ABSTRACT

A process for fractionating agaroid compositions by dissolving the agaroid in a glycol, precipitating a first fraction by cooling and precipitating a second fraction by incorporating a nonsolvent to form two fractions substantially more soluble in water than the initial agaroid. Optionally the solubility of either fraction can be converted to conventional solubilities.

19 Claims, No Drawings

FRACTIONATED AGAROID COMPOSITIONS, THEIR PREPARATION AND USE

This is a continuation-in-part of U.S. application Ser. No. 537,555 filed Jun. 13, 1990, now abandoned.

BACKGROUND OF THE INVENTION

This invention relates to compositions of matter comprising novel fractionated agaroid compounds (including agar and agarose), to methods for the preparation of the compositions and to methods for their use.

Agaroid compounds including agar, agarose, derivatized agarose and depolymerized agarose generally are well known in the art.

The closest known prior art to this invention is European Patent Application EP 0 304 024 published 22 Feb. 1989, (corresponding to U.S. Pat. No. 4,990,611 of 2 Feb. 1991) commonly assigned and invented, which discloses the purification of agar or agarose by means of a glycol solution thereof. More specifically, in the disclosed process: (a) agar or agarose is dissolved in a lower alkylene glycol selected from the group consisting of ethylene glycol, diethylene glycol, propylene glycol, trimethylene glycol, and 1,2-butanediol optionally in the presence of a small amount of water; (b) the solution is heated to a temperature of 50° C. to 130° C.; and (c) upon cooling of the solution to a temperature below 70° C.; (d) a purified agarose (first fraction) precipitates. The precipitate desirably (e) is washed with a volatile organic solvent such as acetone, preferably a lower alkyl alcohol, more preferably methanol, ethanol, or isopropanol, and then dried. The precipitate is disclosed as being extraordinarily soluble in water, in that the water does not need to be heated to dissolve it as in a conventional agarose. There is a disclosure that treatment of the supernatant (still containing a dissolved second agar or agarose fraction) is primarily for the purpose of purifying the glycol for reuse, and that the second agar or agarose fraction present in the supernatant "may either be recovered, as a less pure agarose material, or simply discarded."

The employment of a glycol in conjunction with agar also is taught in U.S. Pat. No. 4,291,025 which discloses a thermally reversible agar gel topical dressing prepared by heating and agitating a mixture of agar, diethylene glycol, and water to solubilize the agar, which is then allowed to cool and form a high strength gel. Formation of a precipitate does not appear to be disclosed. The agar is present in 5–12 wt % and the glycol is not removed but instead comprises from 20 wt % up to a maximum of 75 wt % of the composition. There is a teaching that other polyols such as dipropylene glycol, propylene glycol, or ethylene glycol are not suitable because they do not significantly lower the gelling temperature of aqueous agar gels. Multivalent salts such as sodium borate, potassium borate, potassium sulfate, and zinc sulfate are disclosed as increasing the "toughness" of the gel.

The purification of agarose from crude agar by precipitation from dimethylformamide solvent is disclosed in *Chem. Abstracts* 74:32889r (1971), which is for Japanese Patent document 45-017,180.

The effect of low molecular weight compounds on the properties of aqueous agarose solutions is discussed in *Chem. Abstracts* 105:153437j (1986), which states that glycerin and ethylene glycol aid gel formation but that alcohols, dioxane, and urea inhibit gel formation.

U.S. Pat. No. 3,335,127 discloses employing polyethylene glycol to fractionate an agarose product from an agarose/agaropectin mixture, in which the glycol is contacted with an impure agarose aqueous solution at elevated temperatures to precipitate a purified product.

SUMMARY OF THE INVENTION

This invention affords compositions of matter comprising novel agaroid fractionations, methods for preparing such compositions, and methods for the use of such compositions. The compositions include highly purified agaroids converted to having a normal agarose solubility (i.e. in heated but not in ambient or cold water), dimensionally stable agaroid mats or matrices, water insoluble agaroid beads, and suspended or dissolved agaroid compositions that readily form gels in water at ambient temperature, among others. The inventive methods are improvements over the known method of producing agar or agarose spheroidal microparticles which are extraordinarily soluble wherein an agar or agarose is dissolved in a glycol at a temperature of about 50° C. to 130° C. and the solution is cooled to a temperature below about 70° C. accompanied by up to moderate agitation resulting in precipitate formation, followed by recovery and alcohol washing of the precipitate particles. In broad terms, the improvements of the present invention methods over those of the prior art comprise:

A) expanding the useful starting materials from (a) only agar and native agarose to include one or more agaroids as defined herein and (b) from the previously disclosed glycols;

B) controlling the level of agitation ranging from quiescence up to rapid mixing while cooling the agaroid/glycol solution, thereby causing the dissolved solved agaroid to separate into
   a first fraction (I) agaroid with precipitates upon cooling and has novel properties, and
   a second fraction (II) agaroid which remains dissolved in the glycol supernatant;

C1) forming a coherent agarose gel by admixing unheated water with either or both of the fractions without removal of the glycol solvent; or C2) recovering at least one agaroid fraction from the solution, optionally washing it with an alcohol; and then optionally D) converting a recovered fraction into a material insoluble in unheated water; and/or E) suspending a recovered fraction in a non-aqueous or nonsolvent or redissolving it in a solvent and further treating it.

It will be appreciated that all of the above method steps start with the dissolution of an agaroid in a glycol at elevated temperatures, and that such dissolution per se results in a substantial change of the physical properties of both fractions of the agaroid which is best evidenced by a newly acquired ability to dissolve in water at room temperature. The various further method steps each result in agaroid compositions having unexpected physical properties which are distinct from one another.

When a charged (ionic) agaroid is used as a starting material or when it is desired to precipitate an extraordinarily soluble agaroid without separation into fractions I and II, a glycol soluble salt or salt solution is added prior to the cooling step. Without this salting out procedure, the charged agaroid remains in solution as it retains the ionic properties of the starting material despite the added extraordinarily soluble properties imparted to it when it is dissolved in a heated glycol.

Salting out an ionic macromolecule such as a protein from an aqueous solution (i.e. using ammonium sulfate) or salting out an ionic polysaccharide such as an agaroid using an alcohol in combination with a salt (i.e. isopropanol with NaCl) are known procedures. However, it is not known to salt out an agaroid from a glycol solution. Any known salt or salt solution used in a salting procedure is useful herein, provided that the solvent for the salt, if one is used, is also soluble in the glycol, and that the desired end product is not adversely affected.

DETAILED DESCRIPTION OF THE INVENTION

Other than in the operating examples, or where otherwise indicated, all numbers expressing quantities of ingredients, parameters, or reaction conditions used herein are to be understood as modified in all instances by the term "about".

The present invention affords improvements and variations of the compositions and methods for purifying agar or agarose in U.S. Pat. No. 4,990,611 (and corresponding published European Patent Application 0 304 024), which applications and patents may issue thereon are incorporated herein by reference. Such improvements and variations were unexpected because there was no reason for one skilled in this art to suspect that the second agaroid fraction (from the glycol/agaroid solution supernatant) would itself be useful, or that further chemical and/or physical treatment of the agaroid fractions would result in compositions possessing distinct chemical and/or physical properties. The various compositions' physical attributes permit them to be used in unexpected ways.

Agaroids useful as the solute in this invention include those disclosed in U.S. Pat. No. 4,734,237, and preferably include, but are not limited to: one or more crude, purified or modified agar such as agarose, whether native, purified, derivatized, and/or depolymerized; and mixtures thereof with other (compatible) polymers and additives such as carrageenan. "Derivatized agarose" includes the modified agaroses disclosed in U.S. Pat. Nos. 3,956,273; 4,290,911; and 4,319,975, all of which are incorporated herein by reference. The more preferred agaroids of this invention are agar, agarose, and derivatized agarose, agarose being most preferred. Where a non-derivatized agaroid is employed as the starting material, it is possible to derivatize the end-product.

Glycols useful as the solvent in this invention comprise one or more C1–C4 alkylene glycols, including, but not limited to: ethylene glycol, diethylene glycol, triethylene glycol, trimethylene glycol, propylene glycol, and butylene glycol (1,2-butanediol). It is well recognized that polyethylene glycols, such as triethylene glycol contain other glycols (e.g. ethylene glycol, diethylene glycol and the like).

A factor in some method embodiments of this invention is the degree of agitation to which the solution is subjected while it is cooling. The agitation may range from quiescent (essentially no induced solution motion) to moderate agitation up through high agitation, it being understood that such agitation is along a sliding scale without distinct delimitation between types.

The term "extraordinarily soluble agaroid" (ESA) as used herein refers to an agaroid (particularly agar or agarose) which is soluble in unheated (e.g. ambient or cool) water. This is achieved by dissolution of the agaroid in a glycol at elevated temperatures as disclosed in EP 0 304 024, and therefore ESA is generic to, and a starting point for, the improvements of this invention. Starting with ESA directly contributes to some of the new embodiments of the present invention.

The term "converted agaroid" refers to an ESA which has been functionally converted back to a conventionally soluble agaroid (CSA) in that it is soluble in hot and insoluble in cold water. The method for converting comprises a part of the invention and is effective regardless of the physical form of the agaroid.

"Cross-linking" refers to polymerization of an agaroid fraction sufficiently to render it water insoluble. This can be accomplished by any method known in the art applicable to polyhydroxyl compounds.

EMBODIMENTS AND EXAMPLES OF THE INVENTION

Starting in all instances with an agarose/glycol solution, the following variations in subsequent method of preparation resulted in inventive embodiment compositions having observable distinctive physical properties from one another and from the compositions disclosed in U.S. Pat. No. 4,990,611.

EMBODIMENT (A)—HIGH SURFACE AREA PARTICLES

By varying the rates of cooling and agitation in the formation of the precipitate from that disclosed in the prior art, it unexpectedly was possible to make agaroid particles with considerable higher surface area than known previously. Specifically, the heated glycol/agaroid solution is cooled more rapidly and particularly with vigorous mixing or rapid agitation. As a comparison, the following two examples illustrate the preparation of an ESA according to EP 0 304 024. The known product of these examples (spheroidal microparticles) also comprises the starting material for further embodiments of this invention.

EXAMPLE 1 (Comparison)

PRODUCTION OF SPHEROIDAL ESA MICROPARTICLES

Propylene glycol (100 mL) was introduced into a 250 mL flask, and distilled water (15 mL) was then added to the glycol. 4 g of a commercial grade of agarose (SeaKem,® LE agarose, FMC BioProducts, Rockland, Me.) was slowly added to the mixture with stirring. This stirred suspension was heated at 120° C. for 20 minutes until all of the agarose had dissolved. Heating was then discontinued, and the mixture was allowed to cool slowly to room temperature during a two hour period with gentle to moderate stirring. 20 minutes after cooling was allowed to begin, agarose began to precipitate from the solution. When the temperature of the mixture reached room temperature, it was centrifuged to collect the precipitate. The solid was washed twice with 100 mL of 99% isopropyl alcohol and then was dried in a 55° C. forced air oven. Examination of the solid revealed that it was composed of small, uniformly spherical particles, the majority of which were 1 to 5 microns in diameter. A portion of this solid, purified agarose was placed in stirred water at room temperature. Immediately, the particles began to dissolve in the water, but, before dissolution was complete, a gel began to form on the surface of the particles. Agglomeration of these gel-coated particles followed, preventing further dissolution. This demonstrates that the agarose produced had become so extraordinarily soluble that it could present difficulties in subsequent gel formation.

EXAMPLE 2 (Comparison)

PRODUCTION OF SPHEROIDAL ESA MICROPARTICLES

The following method employed slow to moderate agitation and slow cooling. The laboratory equipment used was:

a Tline™ Laboratory Stirrer Model 101 fitted with a 2 inch (5 cm) diameter three blade mixer; a 4 liter beaker; and a Glas-Col™ heating mantle Model #TM 620.

One hundred twenty grams of SeaKem® LE agarose, (a product of FMC BioProducts, Rockland, Me., U.S.A.) was suspended in a solution in the 4 liter beaker. The beaker was then placed in the heating mantle, covered and the Tline mixer inserted into the suspension.

The heating mantle was set at about 65% power and the mixer at about 45% power. The suspension was heated with mixing until it reached about 110° C. at which point the agarose was entirely dissolved.

The mixing was maintained at about 45% and the heating mantle was turned off. The mixing solution was left to cool in the heating mantle overnight. The next morning (after about 18 hours) the solution had cooled to about 30° C. and the agarose Fraction I had precipitated as 1-5 micron spheroidal micro-particles.

EXAMPLE 3

PREPARATION OF ROUGH, IRREGULAR MICROPARTICLES HAVING INCREASED SURFACE AREA

The following example is characterized by rapid cooling of the agarose/glycol solution accompanied by vigorous agitation, which unexpectedly produced rough, irregular, microparticles with greatly increased surface area.

The equipment used was the same as in Example 2 and an identical agarose/glycol solution was prepared in the same manner. In sharp contrast to the method of Example 2, the beaker and mixer were then removed from the heating mantle and placed in a large deep tray. The tray was deep enough so that when filled with ice water the level of the water was above the level of the agarose/glycol solution in the beaker.

The mixer was turned on full speed and the tray filled with crushed ice and water. The high speed agitation was continued and the ice replenished as necessary until the agarose/glycol had cooled to 20° C. to 30° C. (about 30 minutes). The agarose Fraction I was found to have precipitated as rough, irregular, 1 to 5 micron microparticles having greatly increased surface area over those previously known. It also was found to possess the same extraordinarily soluble (ESA) properties as the prior art.

EMBODIMENT (B)—CONVERTED AGAROID

While the products of prior art Examples 1 and 2 (all of which are ESA) are useful, some problems were presented because of the extraordinary speed with which they formed gels. It was discovered that it is possible to convert the water solubility characteristics of ESA to reverse its unheated water solubility, thus affording a conventionally soluble agaroid (CSA) fraction that is as pure as that achieved in EP 0 304 024, but which is insoluble in unheated water. This overcomes the problem of overly rapid gel formation demonstrated by ESA. Conversion of ESA to conventionally soluble agaroid (CSA) is accomplished by exposure of the ESA to water under conditions in which the ESA cannot dissolve in the water. In a preferred method, ESA is suspended in a mixture containing about 50% of water and 50% of a water-miscible non-solvent for agarose or an agaroid. The non-solvent is preferably an alcohol, most preferably isopropanol, but other alcohols, acetone, and the like can be used, as can mixtures of non-solvents. After standing with or without stirring for a suitable able period, which can be about 30 minutes for micro-particles of Example 1, or longer for larger structures with long diffusion times, the ESA has been converted to CSA and can be washed with alcohol and dried, or diluted into water if desired. Another route is to take ESA which has been washed in alcohol or other non-solvent to remove all glycol, resuspend it in alcohol, and chill to about 5° C. Water chilled to 10° C. or preferably lower is slowly added to the chilled ESA-alcohol suspension with mixing or by diffusion. A possible rate of addition is one volume of water over the course of an hour. For example, ice can be added to the chilled suspension. Progress of the conversion reaction can be conveniently monitored by mixing small samples of the converting mixture with several volumes of water and observing whether or not the particles dissolve.

Upon recovery, it was found that the purified solid is converted to a Conventionally Soluble Agaroid (CSA) while retaining its physical form. The following Example further illustrates the inventive method by which this is achieved.

EXAMPLE 4

A portion of the dried, solid particles produced in prior art Example 1 was added with mixing to a solution of isopropyl alcohol and water (50:50 by volume) at room temperature. This mixture was stirred for 30 minutes, and the solid was recovered by centrifugation. After being washed in 99% isopropyl alcohol, the solid was dried in a 55° C. forced air oven. To demonstrate that the product had been converted from ESA to insoluble, a portion of these solid, nearly spherical particles dispersed easily and completely in the water without any evidence of gelling, dissolution, or agglomeration.

EXAMPLE 5

CONVERTED HIGH SURFACE AREA AGAROSE PARTICLES

Propylene glycol (100 mL) was introduced into a 250 mL flask, and distilled water (15 mL) was then added to the glycol. 4 g of a commercial grade of agarose (Sea® LE agarose, FMC BioProducts, Rockland, Me.) was slowly added to the mixture with stirring. This stirred suspension was heated at 120° C. for 20 minutes until all of the agarose had dissolved. Heating was then discontinued and the flask was removed from the hot plate and immediately placed in an ice-water bath. The mixture was vigorously stirred during the cooling process. The precipitate that formed was recovered by centrifugation, and the solid particles were washed with 99% isopropyl alcohol and then dried in a 55° C. forced air oven. The recovered particles were converted by treatment of these particles by the method previously disclosed with an isopropyl alcohol:water mixture at 4° C. which yielded water-insoluble particles which were then dried in a 55° C. forced air oven. Examination of these particles under a microscope revealed that they had a rough surface and were irregularly shaped. The majority of these water-insoluble particles were 1 to 5 microns in their greatest dimension. This is an improvement over the unconverted otherwise identical particles in that they would no longer dissolve readily in cold water while still affording a high degree of purity, and therefore are useful as chromatography beads.

EXAMPLE 6

USING CONVERTED MICRO BEADS IN HPLC

A 4 mm×75 mm HPLC column was packed with converted agarose micro beads. After equilibrating with TSK buffer, a sample consisting of ATP, tyramine and phenol was run. The flow rate was 0.1 ml/min. The sample separated as tight peaks with the following elution times:

| ATP | 7.25 minutes |
|---|---|
| tyramine | 21.63 minutes |
| phenol | 35.64 minutes |

It is interesting to note that these micro beads have a pore size at least an order of magnitude smaller than any conventional agarose packing material. This means that much smaller molecules can be separated.

EMBODIMENT (C) CROSS-LINKED WATER INSOLUBLE AGAROID

In a further improvement particularly applicable to the products disclosed in EP 0 304 024, but useful for other embodiments of this invention, agaroids may be cross-linked in any manner known in the art applicable to polyhydroxyl compounds to afford water insoluble products. Specifically, the spheroidal microcrystalline particles which precipitate upon slowly cooling the agar or agarose/glycol gel accompanied by slow or moderate agitation when made water insoluble by cross-linking are useful in HPLC and other types of bead chromatography as well as latices when suitably suspended. Agaroids other than agar and agarose may be similarly treated. Particularly advantageous is cross-linking of the rough, increased surface microparticles, which are particularly desirable for the foregoing uses.

Numerous bifunctional reagents are available for cross-linking of agarose and other hydoxy functional polymers. Epichlorohydrin cross-links agarose to form a highly stable matrix (J. Porath, J. C., et al., Chromatog. 60:167 (1971)). Similar products can also be prepared by using 2,3-dibromopropanol (T. Laas, J. Chromatog., 111:373 (1973)).

Bis-epoxides are used to cross-link and will at the same time introduce active groups for immobilization (L. Sundberg, et al., Chromatog. 90:87–98 (1974)). Divinylsulfone is a very reactive compound which rapidly cross-links agarose and also introduces reactive groups (J. Porath, J. C., et al., Chromatog., 103:49 (1975)).

Where cross-linking in aprotic solvents is desirable, bifunctional isocyanates react rapidly with agarose hydroxyl groups when the appropriate catalyst is supplied.

EXAMPLE 7

CROSS-LINKING OF MICROBEADS WITH DVS

Agarose microbeads (20 g) which had been converted to the insoluble form were suspended in 200 ml of 1.0M sodium carbonate. Then 7.7 g of divinylsulfone (DVS) was added and the bead suspension shaken or stirred for thirty minutes at room temperature. The beads were collected by slow speed centrifugation and washed twice with distilled water. The beads were suspended in 1.0M sodium carbonate a second time and 4.05 g of ethylene glycol was added to terminate any reactive vinylsulfone groups. After stirring or shaking at room temperature one hour the beads were collected by centrifugation and washed with distilled water until washes were neutral. Beads were stored as an aqueous suspension or washed with isopropanol and oven dried. The cross-linked beads would not dissolve in boiling water.

EMBODIMENT (D) COHERENT GELS FROM ESA

Suspending the ESA in glycol or other non-solvent permits it to disperse and mix with water before it starts to form a gel. In cool water, below room temperature, the mixing time shortens until the material is very difficult to handle. At room temperature, or preferably at 30° C. to 40° C., the solution stays liquid for 5 to 10 minutes before gelling. Where a derivatized low melting agaroid is the starting material, a gel will not form until the solution is cooled to the gelling temperature of the original material.

This embodiment affords the ability to make gels with all of the components maintained at a relatively low temperature. This is useful for the inclusion of biologicals if they can tolerate the suspending agents. It would also be useful where it is inconvenient or impossible to go through the heating and dissolving required for the agaroid starting material.

Coherent agaroid gels also may be formed in a controlled manner by the addition of water to the agaroid/glycol solution before or after precipitation of the first fraction or, after cooling and removal of the precipitate, to the supernatant containing the second agaroid fraction. Water may be added to the glycol/agarose solution or suspension after it is cooled, preferably also accompanied by agitation. Alternatively, water may be added to the second fraction after removal of the first fraction to form a coherent gel from otherwise waste material.

If the precipitated ESA is suspended in a non-aqueous, water miscible, non-solvent, it will readily dissolve and form a gel in an aqueous system well below the gelling temperature of the resulting gel. Propylene glycol and isopropanol are preferred as the suspending agent but others will work including ethylene glycol, alcohol, acetone, and polyethylene glycol. Glycerin will also work but requires care because glycerin is a solvent for agarose.

Dissolved agarose can be created in a number of ways. If the source agarose is a charged agarose such as DEAE or carboxy methyl agarose, it will dissolve in the glycol but will not precipitate on cooling. Add this solution to an aqueous system and it will form a gel.

Dissolved agarose can also be created by adding a non-aqueous agarose solvent (glycerin) to the glycol/agarose mix.

The properties of the coherent gel will depend in part upon whether it is formed from one or both fractions. The glycol/agarose solution itself therefore was unexpectedly found to afford a useful product forming an agaroid gel without the need for heating it. Examples of this are as follows:

EXAMPLE 8

ESA SOLUTION WITH CHARGED (IONIC) AGAROSE

One gram of derivatized (carboxy methyl) agarose was dissolved in 100 mls of propylene glycol plus 10 mls water in the usual fashion. Because a derivatized agaroid was used, it remained in solution cooling to room temperature. The viscous solution would easily mix with room temperature water and form a gel within a few minutes. The derivatized agaroid could be made to precipitate out in the usual fashion if a salt soluble in the glycol/water mix is added to the solution either during the dissolving step or afterwards.

EXAMPLE 9

ESA SOLUTION BY ADDING GLYCERIN 4 grams of SeaKem® LE agarose was added to a solution of 60 mls propylene glycol, 25 mls glycerin and 15 mls water. The suspension was heated with mixing until it reached about 120° C. and held there until all of the agarose was dissolved. After cooling to room temperature it had formed a very viscous, slightly hazy liquid which would form a gel when added to room temperature water. The glycerin may aid in keeping the agarose in solution.

EXAMPLE 10

ESA SOLUTION BY ADDING PROPYLENE GLYCOL AND GLYCERIN 4 grams of SeaKem® LE agarose was added to a solution of 70 mls propylene glycol and 30 mls glycerin. The suspension was heated with mixing to about 130° C. and held there until all of the agarose had dissolved. On cooling to room temperature with mixing, a fine white precipitate fell out of the solution. This precipitate had all of the qualities of ESA agarose. This example demonstrates that water normally required in a propylene glycol system to get the agarose into solution can be replaced with glycerin.

EXAMPLE 11

PREPARATION OF A COHERENT GEL

A suspension of 4 g of the spherical particles of fractionated agarose (prepared by the method of Example 1) in 100 mL of propylene glycol was prepared by mixing the two components without heating. This suspension (5 mL) was mixed vigorously with 15 mL of distilled water at room temperature. Within a few minutes after stirring had ceased, a firm coherent gel formed. This gel had the appearance and all of the physical properties of a 1% gel of agarose in water made by the usual method which requires boiling the aqueous agarose mixture to obtain complete dissolution.

EMBODIMENT (E)—AGAROID MATRIX

Unexpectedly, it was found that a dimensionally stable agaroid matrix could be formed by cooling the glycol/agaroid solution until the first fraction precipitates, without added agitation. Advantageously, the matrix then may be converted to make it conventionally water soluble. Once converted, the matrix has the properties of a sponge in that it will absorb an unheated liquid, the liquid can be expressed by squeezing, and can then be reabsorbed while the matrix retained its original dimensions. Introduction of the heated glycol/agaroid solution into a cool, nonaqueous, nonagaroid solvent could be used to make hollow fibers, regular fibers or much smaller beads. It was observed that the ability to reabsorb water was not affected by the ion content of the unheated water. Since the matrix is formed by casting, it can have varying thickness, depending upon the amount of agaroid in solution, size of the vessel, etc., and is not limited by any of these factors. When allowed to form of sufficient thickness, the matrix can be cut into blocks or, with appropriate material treatment known in the art, can be dried and cut into fine particles ground into a powder, optionally with subsequent derivatization. The matrix also can be cross-linked as disclosed herein, to render it stable even in heated water. Scanning electron microscope examination has shown the matrix to have pores of 1–20 microns, and the formed cross-linked matrix can be used as a microporous sheet which has the advantage of being 100% agaroid, a bio-gentle material. Prior to cross-linking it can be used to form a gel. The preferred concentrations for formation of the matrix depend on the particular starting agaroid. For conventional agarose (e.g. SeaKem® LE), it is preferred to form the matrix with an initial agaroid concentration of 2% to 8%, preferably 3% to 6%, most preferably 4% to 6%. This gives a workable composition.

The matrix microporous structure gives it tremendous surface area thereby lending itself to use in affinity and ion exchange applications, cell entrapment and electrophoresis. For example, it could be used in clinical diagnostic tests in the following manner. In a spot test or dip stick type format this material will imbibe a known volume of liquid. It will also do a certain amount of filtering as seen in the whole blood example disclosed herein. Reagents could be incorporated into the matrix and a reaction with a known volume of sample could take place right in the matrix. Matrix formation is illustrated by the following examples.

EXAMPLE 12

FORMATION OF A CROSS-LINKED AGAROID MATRIX—SLOW COOLING

Propylene glycol (100 mL) was introduced into a 250 mL flask, and distilled water (15 mL) was then added to the glycol. 4 g of a commercial grade of agarose (SeaKem® LE agarose, FMC BioProducts, Maine) was slowly added to the mixture with stirring. This stirred suspension was heated at 120° C. for 20 minutes until all of the agarose had dissolved. Heating was then discontinued, and the solution was cooled to 100° C. A gel casting cassette consisting of two glass plates separated by a 3 mm thick U-shaped spacer and held together by clamps, was heated to 100° C. The agarose solution was then injected into the hot cassette, and the filled cassette was heated in an oven at 100° C. for an additional 20 minutes. The cassette was removed from the oven and allowed to cool slowly without any agitation or disturbance (i.e. quiescently). After 30 minutes the glycol solution of agarose had solidified into an opaque, white slab which had shrunk sufficiently to pull away from the edges of the cassette. The cassette was then taken apart, and the slab of agarose was gently allowed to slide into a tray containing 99% isopropyl alcohol. The only agitation during this isopropyl alcohol washing operation was a gentle rocking of the tray. After washing with isopropyl alcohol for approximately 17 hours the agarose matrix slab was then converted to cold water insolubility by placing it in a solution of isopropyl alcohol and water (50:50 by volume) at room temperature for 120 minutes. After removal from this solution, the matrix was washed with 99% isopropyl alcohol and dried in a 55° C. oven. After conversion to a cold water insoluble composition, the matrix was cross-linked linked to a water insoluble composition as follows. This matrix was immersed in a 1 mol solution of sodium carbonate in distilled water. Divinyl sulfone (0.39 g per 1.0 g of agarose) was then added to the aqueous solution. The matrix remained immersed in this solution for 2 hours after which it was washed in water and dried in a 55° C. forced air oven. Microscopic examination of this material revealed that it was indeed a porous matrix. This material when placed in water behaves very similarly to a sponge; the imbibed water can then be squeezed from the matrix and reimbibed repeatedly without loss of the matrix structural integrity. Examination via scanning electron microscope shows the matrix to have a structure very similar to conventional microporous membranes with effective pores of a few microns.

EXAMPLE 13

PREPARATION OF A CROSS-LINKED AGAROID MATRIX

A matrix was prepared in the same manner as Example 12 except that the rate of cooling was considerably more rapid.

As in Example 12, the slab of agarose was removed from the cassette and placed in a tray containing 99% isopropyl alcohol for 17 hours. Upon removal from the alcohol the slab was washed three times in tetrahydrofuran, each wash lasting for one hour. The slab was then immersed in tetrahydrofuran, and hexamethylene diisocyanate (0.55 g per 1.0 g of agarose) was then added to the solvent. Two drops of an initiator containing 1000 parts of triethylamine ethylamine and 1 part of stannous chloride were also added to the mixture. The reactants were allowed to remain in contact for 18 hours after which ethylene glycol was added to stop the cross-linking reaction. The matrix was then washed three times in isopropyl alcohol and dried in a 55° C. forced air oven. This matrix had the same properties as the one produced in Example 12 and illustrates another method of cross-linking, without prior conversion to the CSA form.

EXAMPLE 14

WHOLE BLOOD ABSORPTION BY AGAROSE MATRIX

A 1 cm×1 cm×3 cm piece of wet agarose matrix sheet material prepared as in Example 13 had better than 90% of the water removed by squeezing in a press and was placed in approximately 10 mls of whole blood. After about 10 minutes the piece had regained its original shape. Upon examination, it was clear that with the exception of the edges, the agarose matrix had absorbed the plasma while excluding the red cells. This example shows that the matrix will reswell in physiological fluids and also that it will provide a filtering effect. This ability could be useful in the areas of clinical diagnostics.

EXAMPLE 15

PREPARATION OF A CROSS-LINKED AGAROID MATRIX BEAD

Propylene glycol (200 mL) was introduced into a flask, and distilled water (30 mL) was then added to the glycol. This mixture was heated, and 8 g of a commercial grade of agarose (SeaKem® LE agarose, FMC BioProducts, Rockland, Me.) was slowly added to the mixture with stirring. This stirred suspension was heated at 120° C. for 20 minutes until all of the agarose had dissolved. Heating was then discontinued, and the solution was cooled to 100° C. This hot solution was added dropwise to gently stirred isopropyl alcohol at room temperature, forming almost spherical agarose beads which were 3 to 4 mm in diameter. These beads instantly became translucent and within 10 minutes were opaque white. After washing with 99% isopropyl alcohol, these beads were then converted and cross-linked in the manner described in Example 15. They exhibited the same ability to absorb and express water as did the matrix described in Example 15.

EXAMPLE 16

PREPARATION OF MICROPOROUS MATRIX BEADS

Propylene glycol (200 mL) was introduced into a flask, and distilled water (30 mL) was then added to the glycol. 8 g of a commercial grade of agarose (SeaKem® LE agarose, FMC BioProducts, Rockland, Me.) was slowly added to the mixture with stirring. This stirred suspension was heated at 120° C. for 20 minutes until all of the agarose had dissolved. To this hot solution was added 10 g of sodium chloride. This mixture was cooled to 100° C. and then was dropped into gently stirred isopropyl alcohol at room temperature, forming nearly spherical beads which were 3 to 4 mm in diameter.

These beads instantly became translucent and within 10 minutes were opaque white. After being removed from the isopropyl alcohol, the beads were placed in a solution of isopropyl alcohol and water (50:50 by volume) at room temperature in which they were stirred for one hour. During this operation the sodium chloride was dissolved from within the beads. The beads were then washed in isopropyl alcohol and dried in a 55° C. forced air oven. Microscopic examination of these beads revealed that the same microporous porous structure of the beads produced in the previous example predominated; however, larger pores were created when the sodium crystals were dissolved during the isopropyl alcohol/water treatment. These beads may be cross-linked in the manner disclosed herein.

Agaroid fibers were unexpectedly produced while attempting to make very small beads of the matrix material. It is clear that fine fibers can be spun from this material. The resulting non-woven material is useful for bandages, ion exchange, affinity or cell entrapment membranes, and the like.

EMBODIMENT (F)—AGAROID MAT

EXAMPLE 17

PREPARATION OF AN AGAROID MAT

Propylene glycol (100 mL) was introduced into a 250 mL flask, and distilled water (15 mL) was then added to the glycol. 4 g of a commercial grade of agarose (SeaKem® LE agarose, FMC BioProducts, Rockland, Me.) was slowly added to the mixture with stirring. This stirred suspension was heated at 120° C. for 20 minutes until all of the agarose had dissolved. Heating was then discontinued, and the hot solution was sprayed through a heated atomizer, producing thin fibers of agarose which were collected on a fiberglass mesh screen. When a layer of fibers <1 mm thick had been deposited, the screen and the deposited agarose fibers were washed with 99% isopropyl alcohol and were then dried. Microscopic examination of this agarose fiber matrix revealed that it had the appearance of a non-woven mat. This matrix could then be cross-linked by the methods disclosed herein.

EXAMPLE 18

PREPARATION or A CHOPPED MATRIX

Cross-linked agarose beads produced in Example 17 (200 mL) were placed in a Waring blending with 600 mL of water. After this mixture was subjected to the action of the blender at high speed for three minutes, the resulting particles were recovered from the water, washed with 99% isopropyl alcohol, and dried in a 55° C. forced air oven. This treatment yielded coarse, powdered agarose. Tablets of this material weighing 0.03 g each were prepared in a tabletting process. When 1 mL of a saturated, aqueous solution of sodium chloride was placed in contact with one of these tablets, the tablet immediately expanded, broke into small particles, and absorbed all of the liquid, indicating a significantly enhanced absorptive capacity. A tablet placed in a larger volume of water rapidly expanded and broke up into dispersed agarose particles. Tablets prepared in this manner could have application in column packings for chromatography, batch chromatographic media, tablet exploders and cell entrapment. They would be useful anywhere high surface area particles might be used.

EMBODIMENT (G)—AGAROID PARTICLES IN 3-D MATRIX

EXAMPLE 19

PREPARATION OF A THREE-DIMENSIONAL MATRIX CONTAINING AGAROID PARTICLES

A suspension of 20 g of the spherical particles of fractionated agarose (prepared by the method of Example 1) in 100 mL of propylene glycol was prepared by mixing the components without heating. Plugs of 100 ppi polyurethane foam, each 20 mm in diameter and 30 mm long, were each treated with 1 mL of this 20% suspension of agarose in propylene glycol. The treated plugs were massaged to evenly distribute the suspension throughout the polyurethane, and then the plugs were placed in a 55° C. forced air oven to drive off the propylene glycol. Examination of the dried polyurethane foam revealed that finely divided particles of agarose were adhering to the foam. The utility of this agarose-in-foam matrix was demonstrated by placing one of the plugs in a 20 mL syringe. The plunger was then inserted into the syringe, and 10 mL of hot (50° C.) distilled water was drawn into the syringe. This was expelled from the syringe and drawn back into it several times to insure that adequate mixing had occurred. The mixture was finally expelled into a clean beaker where it was allowed to cool. The gel which formed upon cooling to room temperature had the appearance and properties of a 2% agarose gel prepared by conventional methods.

EMBODIMENT (H)—SINTERED AGAROID MAT

EXAMPLE 20

PREPARATION OF A SINTERED MAT

Small, uniformly spherical particles of agarose were prepared by the method of Example 1. After being washed twice with 100 mL of isopropyl alcohol, these particles were resuspended in 50 mL of isopropyl alcohol in a 500 mL beaker. The particles were then allowed to settle on the bottom of the beaker without any further agitation, depositing as a bed of uniform thickness. After all of the particles had been deposited, the beaker was cooled in an ice-water bath. Slowly, 60 mL of ice-cold water was added to the beaker in a manner to avoid disturbing the bed of particles. After all of the water had been added, the beaker was kept in the ice-water bath for two hours before the aqueous alcohol was decanted. Examination of the solid that was removed from the bottom of the beaker revealed that it was a rigid sheet of agarose about 2 mm thick. Microscopic examination further revealed that this sheet was highly porous. The treatment with water had sintered (i.e. fused) the spherical particles together to create this sheet.

EMBODIMENT (I) AGAROID BEADS

ESA is particularly useful if it is desired to entrap a biological material in an agaroid bed without exposing that material to the normal agaroid solution temperatures.

High agaroid concentration beads are possible by this method. Unlike normal methods which require the agaroid (e.g. agarose) to be in solution just prior to the bead making process. ESA is precipitated and therefore there are not the same viscosity restraints that are imposed on the conventional systems. For this reason, agaroid beads of 20% to 30% agaroid to water concentration are theoretically possible.

When desired, agaroid beads can be made ate. 4° C. This is possible because the ESA is not dissolved and then gelled, but rather because the water is slowly inwardly diffused. It was unexpected to be able to make an agarose bead with all reagents held at a temperature as low as 4° C. in view of known agarose behavior.

EXAMPLE 21

PREPARATION OF AN AGAROID BEAD

Spherical particles of fractionated agarose were suspended in propylene glycol. This suspension was added dropwise to 1 L of water at room temperature. Upon contacting the water, the drops of the suspension formed almost spherical beads which were approximately 3 to 4 mm in diameter. Inspection of these beads after being in the water for a few minutes revealed that they were composed of an agarose gel shell surrounding the still-liquid propylene glycol suspension of agarose. A residence time of approximately 30 minutes in the water converted these beads into an agarose gel having no liquid contained therein.

EMBODIMENT (J)—AGAROID ENCAPSULATION

The use of ESA is the only known way to create agarose capsules. It is believed to be the only known way to make capsules with a thermally reversible gel system that does not require counter ions or cross-linking agents. This is a very gentle system which creates robust capsules, and may have potential use in many encapsulation applications, including enteric coatings where the capsule is neither converted nor cross-linked.

EXAMPLE 22

PREPARATION OF A BEAD WITH AGAROID SHELL

A suspension of spherical particles of fractionated agarose in propylene glycol was prepared by the method of Example 21. Small (2 to 3 mm) beads of 1.25% sodium alginate (Bellco) were introduced into this suspension which was gently stirred. Stirring continued for one hour after which the beads were removed from the propylene glycol. After washing the beads with 99% isopropyl alcohol, they were examined with a microscope. This examination revealed that the sodium alginate beads had acquired a shell of agarose. Some of these beads were placed in a 1 mol solution of sodium citrate to dissolve the alginate gel. This mixture was gently stirred for one hour at room temperature. Microscopic examination revealed that the alginate had completely dissolved, leaving a shell of agarose gel surrounding an aqueous liquid core. The agarose shell exhibited significant strength and physical integrity.

EXAMPLE 23

PREPARATION OF AGAROSE SHELL AROUND BEADS

The procedure of Example 22 was followed except that the sodium alginate beads were removed from the propylene glycol suspension immediately after being introduced into it.

These beads were then placed in water for a few minutes. After being removed from the water, these beads were examined and were found to have acquired a robust coating of an agarose gel.

EXAMPLE 24

PREPARATION OF AN AGAROSE SHELL AROUND INERT PARTICULATE MATERIAL

Agarose capsules were made in a fashion similar to the preceding example with the exception that small glass beads were included in the alginate beads. After dissolving the alginate beads, it was seen that the small glass beads were encapsulated within the agarose shells.

EXAMPLE 25

PREPARATION OF AGAROSE SHELL AROUND BEADS

Sodium alginate (2 to 3 mm beads) were rolled in dry spherical particles of agarose produced by the method of Example 1 until they were completely and uniformly coated with the agarose. These coated beads were then introduced into a beaker containing water at room temperature. After being in the water for a few minutes, these beads were removed and were examined microscopically. This examination revealed that each bead was completely coated with a shell of agarose gel that appeared to be rough and granular.

EMBODIMENT (K) LOTION BASE

The following is illustrative of a manner in which the compositions of matter of this invention may be used beyond the expected applications in biotechnology.

EXAMPLE 26

GLYCOL/AGAROID SUSPENSION LOTION BASE

A few drops of a room temperature suspension of glycol/agarose in propylene glycol was rubbed into the palm of one hand. As it was rubbed in, the milky solution cleared. The solution rubbed in easily and within minutes had formed a slightly tacky clear film on the skin. The hand was dipped into water and the film almost immediately turned into a thin gel which could be stripped from the skin.

I claim:

1. A process for converting an extraordinarily soluble agaroid, precipitated from a glycol solution and which is soluble in water at temperatures below the gelling temperature of an aqueous gel made from said extraordinarily soluble agaroid, to a converted agaroid of the same physical shape and form which has a minimum dissolution temperature in water higher than the melting temperature of an aqueous gel made from said extraordinarily soluble agaroid comprising exposing the extraordinarily soluble agaroid to water under conditions which inhibit the dissolution of the extraordinarily soluble agaroid.

2. The process of claim 1 wherein the extraordinarily soluble agaroid is converted into a converted agaroid by exposing the extraordinarily soluble agaroid to a solution containing about 50% water and 50% of a water miscible, non-solvent for the extraordinarily soluble agaroid, under conditions in which the extraordinarily soluble agaroid cannot dissolve.

3. The process of claim 2, wherein the non-solvent for the extraordinarily soluble agaroid is selected from the group consisting of isopropanol and acetone.

4. The product of claim 2 produced from an ESA which was produced by fractionating an agaroid.

5. The process of claim 1 wherein the extraordinarily soluble agaroid is converted to a converted agaroid by suspending the extraordinarily soluble agaroid in chilled alcohol and slowly exposing the suspension to water chilled to about 10° C. or less.

6. The process of claim 2 wherein the non-solvent is selected from the group consisting of a water miscible alcohol and acetone.

7. The product of claim 6 produced from an ESA which was produced by fractionating an agaroid.

8. The product of claim 5 produced from an ESA which was produced by fractionating an agaroid.

9. The product of claim 1 produced from an ESA which was produced by fractionating an agaroid.

10. The process of claim 1, wherein the extraordinarily soluble agaroid is converted to a converted agaroid by removing all glycol from an extraordinarily soluble agaroid, re-suspending the extraordinarily soluble agaroid in an alcohol, other than glycol, chilling the suspension to 50° C., then adding water chilled to 10° C. or lower.

11. The process of claim 10, wherein the water is added by diffusion.

12. In a process for dissolving agaroid compositions in a glycol comprising dissolving an agaroid in the glycol at a temperature of about 50° C.–130° C. and maintaining the solution at or near the dissolution temperature to maintain the agaroid composition in solution, the improvement comprising adding glycerin to the solution prior to cooling to result in an agaroid solution at temperatures below the precipitation temperature of the agaroid solution without the glycerin.

13. The process of claim 12 wherein the glycerin is present in an amount equal to 5% to 50% by weight.

14. The product agaroid solution of claim 12.

15. The product agaroid solution of claim 13.

16. In a process for preparing a conventionally soluble agaroid composition comprising dissolving an agaroid in a glycol at a temperature of about 50° C.–130° C.; cooling the solution in a quiescent state to a sufficiently lower temperature to result in a dimensionally stable micro-porous agaroid matrix as a first precipitate; and then exposing that precipitate to water under a condition that would inhibit the dissolution of the first precipitate, thereby converting the first precipitate into a conventionally soluble agaroid matrix.

17. The process of claim 16 wherein the first precipitate is converted into the conventionally soluble agaroid matrix by exposing the first precipitate to a solution containing about 50% water and 50% of a water miscible, non-solvent for the first precipitate.

18. The product of claim 16 produced from an ESA which was produced by fractionating an agaroid.

19. The product of claim 17 produced from an ESA which was produced by fractionating an agaroid.

* * * * *